United States Patent
Iyengar et al.

(10) Patent No.: US 9,376,379 B2
(45) Date of Patent: Jun. 28, 2016

(54) PROCESS FOR THE SYNTHESIS OF TETRAFLUOROETHANESULFONIC ACID

(71) Applicant: SRF LIMITED, Gurgaon (IN)

(72) Inventors: Sarathy Iyengar, Tamil Nadu (IN); Radha Kumaraswamy, Tamil Nadu (IN); Mariano Patrick Philiphs, Tamil Nadu (IN); Vardaraj Ganeshan, Tamil Nadu (IN); Rahul Saxena, Tamil Nadu (IN); Rajdeep Anand, Tamil Nadu (IN)

(73) Assignee: SRF Limited (IN)

( * ) Notice: Subject to any disclaimer, the term of this patent is extended or adjusted under 35 U.S.C. 154(b) by 0 days.

(21) Appl. No.: 14/418,223

(22) PCT Filed: Jul. 29, 2013

(86) PCT No.: PCT/IN2013/000468
§ 371 (c)(1),
(2) Date: Jan. 29, 2015

(87) PCT Pub. No.: WO2014/020614
PCT Pub. Date: Feb. 6, 2014

(65) Prior Publication Data
US 2015/0259281 A1   Sep. 17, 2015

(30) Foreign Application Priority Data

Jul. 30, 2012  (IN) ............ 2345/DEL/2012

(51) Int. Cl.
*C07C 303/22* (2006.01)
(52) U.S. Cl.
CPC .................. *C07C 303/22* (2013.01)
(58) Field of Classification Search
None
See application file for complete search history.

(56) References Cited

U.S. PATENT DOCUMENTS 2,403,207 A * 7/1946 Barrick ............ 562/113

FOREIGN PATENT DOCUMENTS

| CN | 1097191 | * | 1/1995 |
| CN | 102070494 | | 5/2011 |

OTHER PUBLICATIONS

International Search Report and the Written Opinion of the International Searching Authority, PCT/IN2013/000468, SRF Limited, Jan. 24, 2014.
Machine Translation of CN102070494, Preparation method of fluorine-containing sulfoacid, Wei et al., May 25, 2011, 7 pages.
Machine Translation of CN1097191, Synthesizing method for fluorohydrocarbyl-sulfonate, Huang et al., Jan. 11, 1995, 19 pages.

* cited by examiner

Primary Examiner — Karl J Puttlitz
(74) Attorney, Agent, or Firm — McDonald Hopkins LLC

(57) ABSTRACT

The present invention provides a process for preparation of tetrafluoroethanesulfonic acid.

8 Claims, No Drawings

PROCESS FOR THE SYNTHESIS OF TETRAFLUOROETHANESULFONIC ACID

FIELD OF THE INVENTION

The present invention provides a process for preparation of tetrafluoroethanesulfonic acid.

BACKGROUND OF THE INVENTION

The halogenated compounds, such as fluoro alkane sulfonic acids, have wide applications as super acids.

The U.S. Pat. Nos. 7,683,209 and 7,897,807 provide a process for preparing hydrofluoroalkanesulfonic acid by reacting fluoro olefin with sulfite in an aqueous solution adjusted to about pH 4 to pH 12. The water is removed from the solution to get a solid which is treated with oleum. The hydrofluoroalkanesulfonic acid is distilled therefrom.

The Journal of Organic Chemistry, 2008, 73, 711-714 provides a process for the preparation of potassium 1,1,2,2-tetrafluoroethanesulfonate from tetrafluoroethylene in a buffered aqueous solution of potassium sulfite and bisulfite and then converted to 1,1,2,2-tetrafluoroethane sulfonic acid in 90% overall yield by distillation from oleum solution.

The GB Patent No. 0,579,897, U.S. Pat. No. 2,403,207 and Journal of Organic Chemistry, 1949, 14, 747-753 also provide process(s) for preparation of tetrafluoroethanesulfonic acid or its salt.

The above cited prior art processes for preparation of tetrafluoroethanesulphonic acid proceed through hydrolysis of tetrafluoroethanesulphonate salt using sulfuric acid or oleum. The present inventors have observed that since the boiling point of tetrafluoroethanesulfonic acid is in the range of 210°-211° C., the tetrafluoroethanesulphonic acid has a strong affinity to stay in the pool of sulfuric acid when subjected to hydrolysis using either sulfuric acid or oleum. Therefore, stringent reaction conditions like high temperature and vacuum is required to recover the acid from the hydrolysis mixture. Moreover, it is not possible to extract the entrapped acid from the pool completely. Furthermore, such process is not feasible at industrial scale due to high incurring cost by the use of exotic materials of construction such as Inconel, Monel to name a few. Additionally, the use of dilute sulfuric acid (30-35% concentration) for hydrolysis of alkali metal salt of tetrafluoroethanesulfonic acid has a drawback of repeated ethereal extractions.

Thus, there is need in the art for a simple, cost effective and commercially viable method to prepare tetrafluoroethanesulfonic acid which obviates the use of high boiling sulfuric acid and harsh reaction conditions.

SUMMARY OF THE INVENTION

In an aspect, the present invention provides a process for the preparation of tetrafluoroethanesulfonic acid, comprising;
a) treating alkali metal salt of tetrafluoroethanesulfonic acid in an aliphatic alcohol solvent with dry hydrochloric acid,
b) treating mixture of step a) with water to obtain tetrafluoroethanesulfonic acid monohydrate, and
c) dehydrating tetrafluoroethanesulfonic acid monohydrate to obtain tetrafluoroethanesulfonic acid.

DETAILED DESCRIPTION OF THE INVENTION

In an embodiment, the present invention provides a process for preparation of tetrafluoroethanesulfonic acid, comprising;
a) treating alkali metal salt of tetrafluoroethanesulfonic acid in an aliphatic alcohol solvent with dry hydrochloric acid,
b) treating mixture of step a) with water to obtain tetrafluoroethanesulfonic acid monohydrate, and
c) dehydrating tetrafluoroethanesulfonic acid monohydrate to obtain tetrafluoroethanesulfonic acid.

The alkali metal salt of tetrafluoroethanesulfonic acid may be prepared by any method known in the art, for example, by method known in U.S. Pat. No. 2,403,207.

The alkali metal salt of tetrafluoroethanesulfonic acid is selected from lithium tetrafluoroethanesulfonate, sodium tetrafluoroethanesulfonate, potassium tetrafluoroethanesulfonate, rubidium tetrafluoroethanesulfonate and cesium tetrafluoroethanesulfonate. The aliphatic alcohol solvent is selected from methanol, ethanol, n-propanol, 2-propanol, 1-butanol and 2-butanol or mixture thereof.

The step a) may be carried out at a temperature of about 10° C. to about 30° C., for example, about 15° C. to about 20° C., for about 30 minutes to about 12 hours, for example for about 1 hour to about 3 hours.

The dry hydrochloric acid may be gaseous state.

The dehydration of tetrafluoroethanesulfonic acid monohydrate to obtain tetrafluoroethanesulfonic acid is carried out in the presence of thionyl chloride. The dehydration may be carried out at a temperature of about 15° C. to about 120° C., for example, about 25° C. to about 80° C. for about 1 hour to about 20 hours, for example for about 3 hours to about 4 hours.

The tetrafluoroethanesulfonic acid may be isolated by layer separation, distillation, decantation and evaporation or mixture thereof. The tetrafluoroethanesulfonic acid may be further purified by distillation.

The tetrafluoroethanesulfonic acid, so obtained in step c), has purity greater than 98%, for example, greater than 98.5% by titration method.

While the present invention has been described in terms of its specific embodiments, certain modifications and equivalents will be apparent to those skilled in the art and are intended to be included within the scope of the present invention.

EXAMPLES

Example 1

Preparation of Tetrafluoroethanesulphonic Acid

1a) The sodium sulphite (151 g) was dissolved in water (500 mL) and taken in a 1000 mL Hastelloy reactor. Tetrafluoroethylene (100 g) was added to the reactor at −130° C. The temperature of the reactor was increased to 120° C. and maintained at 120° C. for 12 hours. The reactor was cooled to 25° C. and unreacted tetrafluoroethylene was vented off. The water of the reaction was removed from reaction mixture by azeotropic distillation to obtain a reaction mass. The reaction mass was extracted with hot ethanol using soxhlet apparatus. The ethanolic solution was concentrated to obtain pure sodium tetrafluoroethane sulfonate (50 g).

The sodium tetrafluoroethane sulfonate (50 g) and methanol (96 g) were taken in a reaction vessel and the mixture was cooled to 15° C. The dry hydrochloric acid (73 g, 35%) was passed through the mixture for 45 minutes. The mixture was further stirred for 30 minutes, filtered and washed with methanol (15 g). The filtrate (125 g) was added to water (125 g) and mixture was distilled using one foot column. The distillate (182 g) was obtained at 60° C./10 mm Hg.

Yield: 56 g (Moisture content: 30.52%; Tetrafluoroethanesulphonic acid—69.3%)

The tetrafluoroethanesulfonic acid monohydrate (56 g) was taken in a reaction vessel and thionyl chloride (116 g) was added drop-wise at 25° C. over a period of 3 hours. The temperature of reaction mixture was raised to 80° C. and the mixture was refluxed for 30 minutes. The mixture was cooled to 40° C. The crude material (38 g) was subjected to distillation under vacuum.

Yield: 33 g
Purity (%): 99

1b) The sodium sulphite (201 g) was dissolved in water (600 mL) and taken in a 1000 mL Hastelloy reactor. Tetrafluoroethylene (150 g) was added to the reactor at −130° C. The temperature of the reactor was increased to 120° C. and maintained at 120° C. for 12 hours. The reactor was cooled to 25° C. and unreacted tetrafluoroethylene was vented off. The water of the reaction was removed from reaction mixture by azeotropic distillation to obtain a reaction mass. The reaction mass was extracted with hot ethanol using soxhlet apparatus. The ethanolic solution was concentrated to obtain pure sodium tetrafluoroethane sulfonate (100 g).

The sodium tetrafluoroethane sulfonate (100 g) and methanol (140 g) were taken in a reaction vessel and the mixture was cooled to 15° C. The dry hydrochloric acid (100 g, 35%) was passed through the mixture for 45 minutes. The mixture was further stirred for 30 minutes, filtered and washed with methanol (15 g). The filtrate (244 g) was added to water (125 g) and mixture was distilled using one foot column. The distillate (319 g) was obtained at 60° C./10 mm Hg.

Yield: 96 g (Moisture content: 23.30%; Tetrafluoroethanesulphonic acid—72.3%)

The tetrafluoroethanesulfonic acid monohydrate (96 g) was taken in a reaction vessel and thionyl chloride (160 g) was added drop-wise at 25° C. over a period of 3 hours. The temperature of reaction mixture was raised to 80° C. and the mixture was refluxed for 30 minutes. The mixture was cooled to 40° C. The crude material (69 g) was subjected to distillation under vacuum.

Yield: 64 g
Purity (%): 98.5

We claim:

1. A process for preparation of tetrafluoroethanesulfonic acid, comprising
   a) treating alkali metal salt of tetrafluoroethanesulfonic acid in an aliphatic alcohol solvent with dry hydrochloric acid,
   b) treating mixture of step a) with water to obtain tetrafluoroethanesulfonic acid monohydrate, and
   c) dehydrating tetrafluoroethanesulfonic acid monohydrate to obtain tetrafluoroethanesulfonic acid.

2. The process of claim 1, wherein alkali metal salt of tetrafluoroethanesulfonic acid is selected from lithium tetrafluoroethanesulfonate, sodium tetrafluoroethanesulfonate, potassium tetrafluoroethanesulfonate, rubidium tetrafluoroethanesulfonate and cesium tetrafluoroethanesulfonate.

3. The process of claim 1, wherein aliphatic alcohol solvent is selected from methanol, ethanol, n-propanol, 2-propanol, 1-butanol and 2-butanol or mixture thereof.

4. The process of claim 1, wherein step a) is carried out at a temperature of about 10° C. to about 30° C.

5. The process of claim 1, wherein dehydration of tetrafluoroethanesulfonic acid monohydrate is carried out in the presence of thionyl chloride.

6. The process of claim 1, wherein dehydration is carried out at a temperature of about 15° C. to about 120° C.

7. The process of claim 1, wherein tetrafluoroethanesulfonic acid has purity greater than 98%.

8. The process according to claim 7, wherein tetrafluoroethanesulfonic acid has purity of at least 98.5%.

* * * * *